United States Patent [19]
Wladimiroff et al.

[11] 4,329,316
[45] May 11, 1982

[54] INSTRUMENT FOR CHEMI- OR BIOLUMINESCENT ANALYSIS

[76] Inventors: Wladimir Wladimiroff, Kyrkbacken 27, Solna S-17150; Gabor Merenyi, Bjornstigen 28, Solna S-17172, both of Sweden

[21] Appl. No.: 190,673
[22] PCT Filed: Jun. 15, 1979
[86] PCT No.: PCT/SE79/00136
§ 371 Date: Feb. 13, 1980
§ 102(e) Date: Feb. 13, 1980
[87] PCT Pub. No.: WO80/00098
PCT Pub. Date: Jan. 24, 1980

[30] Foreign Application Priority Data
Jun. 19, 1978 [SE] Sweden ............... 7806999

[51] Int. Cl.$^3$ ............ G01N 21/26; G01N 21/52; G01J 1/54; B01F 5/18
[52] U.S. Cl. ............... 422/52; 23/232 R; 422/83
[58] Field of Search ............ 422/52, 68, 83; 23/232 R

[56] References Cited
U.S. PATENT DOCUMENTS
3,528,779 9/1970 Fontijn .................. 422/52 X
3,690,837 9/1972 Witz et al. ............. 422/52
3,692,485 9/1972 Neti et al. ............. 422/52 X
3,746,514 7/1973 Colvin et al. ........... 422/52
3,963,928 6/1976 Zolner ................. 422/52 X FOREIGN PATENT DOCUMENTS
1353722 5/1974 United Kingdom .
1456962 12/1976 United Kingdom .

*Primary Examiner*—Ronald Serwin
*Attorney, Agent, or Firm*—Pollock, Vande Sande & Priddy

[57] ABSTRACT

The invention relates to an instrument for chemi- or bioluminescent analysis of the concentration of a constituent of a sample gas ($G_1$) which in a reaction chamber (C) reacts with a liquid reagent ($R_1$) in a luminescent manner. The liquid reagent ($R_1$) is ejected into the reaction chamber (C) by ejection means. The sample gas ($G_1$) can be used as propellant in the ejection means (E) sucking the liquid reagent ($R_1$) into the propellant and as an aerosol be sprayed into the reaction chamber. Carefully mixed with the sample gas, it generates chemiluminescent radiation ($L_1$, $L_2$) in the field of view of a photodetector (D). The propellant ($G_1$) can also be prepared so that either heating or cooling occurs on expansion in the reaction chamber (C). By providing walls of the reaction chamber with reflecting layers, the main portion of the luminescent radiation reaches the detector (D).

**18 Claims, 3

INSTRUMENT FOR CHEMI- OR BIOLUMINESCENT ANALYSIS

TECHNICAL FIELD

This invention relates to an instrument for the generation and detection of bio- or chemiluminescent radiation. This is achieved by bringing together in a reaction chamber two or more gaseous or liquid substances into the field of view of a photodetector means; at least two of these substances yield luminescence upon reacting and at least one of them is a gas.

BACKGROUND ART

For the quantitative analysis of small amounts of gaseous substances several methods are used at present, such as spectrophotometry, fluorimetry, gas-chromatography and galvanometry. All of these require relatively expensive equipment. Particularly in cases where an accurate determination of very small amounts of i.e. gaseous pollutants (with hygienic limits set at 1 ppm or lower) is required, the available instruments tend to be both costly and bulky. Due to a growing demand for a better working environment, a need has long been felt for reliable, simple, cheap and in particular, sensitive measuring devices for the quantitative determination of gaseous or gasborne pollutants with concentrations ranging from 10 ppm down to thousandths of ppm.

It is known (i.e. Anal. Chem., 45, 443A (1973)) that a large number of gaseous substances can be accurately determined by means of chemiluminescent reactions. Such reactions generate light, the intensity of which is directly proportional to the concentration of the reacting substances. If during the reaction the luminescent substance is in excess, the light intensity is directly proportional to the concentration of the substance investigated in the sample; thus a simple measurement of light intensity yields an accurate determination of the sample concentration. The radiation can be generated in any of the visible, ultraviolet and infrared spectral regions.

Generally, a luminescent substance can be either a solid, a liquid or a gas. When a gaseous sample reacts with a liquid reagent, the light generation will be proportional to the area of the gas-liquid interface.

In a known device this is achieved by adsorbing the reagent on a gel and passing the gaseous sample over the surface of the gel (Geophys. Res. 65, 3975 (1960)). The disadvantage of this method (as that of other devices in which a gaseous sample is bubbled through a liquid reagent) is the relatively small size of the gas-liquid interface. When the objective is to continuously determine a gaseous pollutant such as ozone, continuous blowing of the sample against the reagent in the gel or bubbling it through the reagent causes the latter to successively change its concentration as a result of evaporation and reaction with the sample, resulting in an unsatisfactory accuracy of the analysis.

If both reagent and sample are gaseous a number of known devices are available where both gases mix and react to yield chemiluminescence. In the British Pat. Nos. 1,341,346 and 1,353,722 two different reaction chambers are described, in which the gases are mixed in front of a photomultiplier. These devices can only be used for purely gaseous components.

In the American Pat. No. 3,998,592 a thermoelectric heat-pump is used for simultaneous heating of the reaction cell and cooling of the photomultiplier. This device is also intended for gaseous components only. Furthermore, the thermoelectric heat-pump only yields a certain preset temperature difference between the hot and the cold side. As a rule, the photomultiplier has to be cooled further—either directly or by extracting more heat from the hot side of the thermoelectric heat-pump. With some bio-or chemiluminescent systems better light yields are obtained at temperatures below ambient temperature; in such cases the above-mentioned device is not applicable.

DISCLOSURE OF THE INVENTION

The present invention relates to an instrument for bio- or chemiluminescent analysis without the above-mentioned limitations and in which the concentration of a sample gas is measured in a reaction chamber in the field of view of a photodetector means, reacting in a luminescent manner with a liquid reagent from a reagent container. Said instrument comprises means for ejecting said liquid reagent into said reaction chamber in the form of aerosol particles and means for providing a flow of said sample gas to the reaction chamber at least at atmospheric pressure. By causing the sample gas flow to be pulsed with arbitrarily presettable pulse duration and intervals, two advantages are gained. On the one hand a higher sample gas pressure can be used, resulting in a considerably higher luminescent intensity and on the other hand, a lower consumption of the reagent occurs due to the intermittence. The ejector means may use the sample gas as a propellant in such a way that the liquid reagent via one or several pipes is arranged to be sucked into the propellant gas jet by the ejection effect and converted into an aerosol.

In some cases, an inert gas may serve as propellant. By choosing a carrier-gas with a high inversion temperature, such as $N_2$, the gas is cooled on expansion outside the ejector. If heating is desired instead, a carrier-gas with a low inversion temperature, such as $H_2$, can be used.

The ejector device is preferably arranged to be adjustable with respect to the size of the aerosol particles. The latter should of course be as small as possible in order for the total gas-liquid interface to be as large as possible. A radius of $10^{-3}$ cm for the aerosol particles will give a total surface of 3000 $cm^2$ for 1 $cm^3$ of liquid. Adjustment can be achieved by the positioning of the ejector tube in the ejector nozzle.

It can also be advantageous to design the liquid reagent tube (tubes) entering the ejector (ejector tubes) in the form of capillaries, at least in some part of the tube. In this way, the liquid substance will now flow back beyond the capillary. The time needed for the carrier-gas to suck up liquid from the capillary to the ejector nozzle can be made equal to the time needed for the carrier-gas to flush the reaction chamber and the detector window before the liquid reaches the ejector and the start of the chemiluminescent reaction.

If the light generation in the reaction is weak, the light flux to the detector can be increased by making the walls of the chamber reflecting. The detector is placed on the outside of the window or on a transparent part of the reaction chamber.

In order to prolong the usage of the liquid reagent it is advantageous to drain the reagent back into the reagent container by means of an electronically controlled valve. This is done as long as the detector does not yield a signal or if the signal has a lower amplitude than a preset threshold value. Otherwise the reagent is channelled into a container for consumed reagent. One advantage with said method is that the reproducibility is considerably increased due to the fact that only fresh reagent will participate in the luminescent reaction.

If substances occur whose detection is not required but which also yield chemiluminescence with the particular reagent being used, the photodetector unit may be arranged to contain two or more detector elements each of which is supplied with a transmission filter for different wavelengths or wavelength bands. The relation between the signal amplitudes then decides whether the detection should result in an alarm or not.

In some cases it can be advantageous to keep the detector (if arranged within the reaction chamber) or the detector window, free of liquid substances. This can be achieved by means of a gas- or air curtain.

BRIEF DESCRIPTION OF THE DRAWINGS

The invention is described in more detail below with reference to the enclosed FIGS. 1-3. FIGS. 1 and 2 show an embodiment of the invention, of which FIG. 1 shows a block-diagram, while FIG. 2 shows an intersection of an enlarged drawing of the reaction chamber with the ejector device. It also shows a photodetector means mounted onto the reaction chamber.

In FIG. 1 a gaseous sample $G_1$ in the form of ambient air is arranged to be sucked through a filter F by means of a pump P, which subsequently compresses the sample $G_1$ in a sample volume V. When a magnetic valve $M_1$ opens, the sample (which in the present case is the propellant gas as well) flows with high speed through a nozzle H surrounding an ejection tube K (FIG. 2) in the ejector device E and in so doing sucks up liquid reagent $R_1$ from the reagent container $S_1$ by means of the ejector effect. The propellant gas $G_1$ thus draws the liquid reagent $R_1$ into the gas-jet, here consisting of ambient air. The reagent $R_1$ is dispersed and is sprayed in the form of an aerosol into the reaction chamber C. The light generated by luminescence partly falls directly $L_1$ (FIG. 2) onto the detector unit D and partly on the reflecting walls. After having been reflected one or more times $L_2$, the light reaches the detector D. The walls of the reaction chamber C are coated with a reflecting layer B. The major part of the reagent is led either through a magnetic valve $M_2$ back to the reagent container $S_1$ or in cases when the measured light exceeds a preset threshold value on the signal processing unit A, is led to a container for waste reagent $S_2$. The result of the measurement is presented by a display unit N. This measuring sequence is repeated after a predetermined interval.

FIG. 2 shows the reaction chamber C with ejection means E and detector means D. The ejector tube K is adjustable along the length direction to minimize the drop size. The wall T onto which the detector means D is arranged is transparent for the radiation in question. Furthermore, the reaction chamber is provided with drain passages U and W for gas and liquid respectively.

FIG. 3 is a front view of a possible embodiment of an ejecting means provided with two ejector tubes K, one for reagent $R_1$ and one for gas $G_2$. One advantage of the embodiment of FIG. 3 is that, apart from being used with liquid reagent $R_1$ it also can be used for gaseous reagent $G_2$. Provided an inert propellant gas $G_1$ is used, both a liquid reagent $R_1$ and sample gas $G_2$ can be sucked through ejector tubes K. This renders the instrument very flexible. In the case where the propellant gas $G_1$ sucks in another gas $G_2$ (eventually together with a liquid $R_1$) by means of the ejector effect, said other gas $G_2$ can be samples of ambient air.

We claim:

1. An apparatus for luminescent analysis of the concentration of a constituent in a sample gas, comprising:
- a reaction chamber;
- means for ejecting into said chamber a quantity of liquid reagent in the form of aerosol liquid particles;
- means for providing a flow of sample gas into said chamber at least at atmospheric pressure;
- means for detecting luminescent light produced by reaction of said sample gas with said aerosol liquid particles; and
- means for collecting used liquid reagent.

2. Apparatus according to claim 1, in which said means for providing a flow of sample gas to said reaction chamber is arranged to provide said gas flow in pulses with predetermined duration and pressure.

3. Apparatus according to claim 1 or claim 2, in which said means for ejecting uses the sample gas as a propellant.

4. Apparatus according to claim 2, in which said means for ejecting uses a gas mixture as a propellant gas with the sample gas as one of the components.

5. Apparatus according to claim 4, in which said sample gas is prepared to either increase or decrease its temperature on expansion.

6. Apparatus according to any one of claims 1, 2, 4, or 5, in which said means for ejecting comprises means for adjusting the aerosol particle size.

7. Apparatus according to claim 1, in which the walls of said reaction chamber are made reflective to the luminescent light.

8. Apparatus according to claim 1, in which said means for detecting comprises two or more detector units, each provided with a transmission filter for a different wavelength or wavelength band, said detector units being electrically connected to a signal processing means.

9. Apparatus according to claim 1, in which said means for collecting used liquid reagent is arranged to lead the used liquid reagent from said reaction chamber to a reagent container as long as the signal amplitude from said means for detecting is lower than a predetermined value, and arranged to lead said used liquid reagent from said reaction chamber to a means for receiving waste reagent liquid if the signal amplitude reaches or exceeds said predetermined value.

10. A method of luminescent analysis of the concentration of a constituent in a sample gas, comprising the steps of:
- providing a reaction chamber;
- ejecting into said chamber a quantity of liquid reagent, in the form of aerosol liquid particles;
- providing a flow of sample gas at least at atmospheric pressure into said chamber, whereby said aerosol liquid particles and said sample gas react to produce luminescence;
- detecting said luminescence to determine the concentration of the constituent; and
- collecting used liquid reagent.

11. A method according to claim 10, wherein said flow of sample gas is provided in pulses with predetermined duration and pressure.

Figure 1:
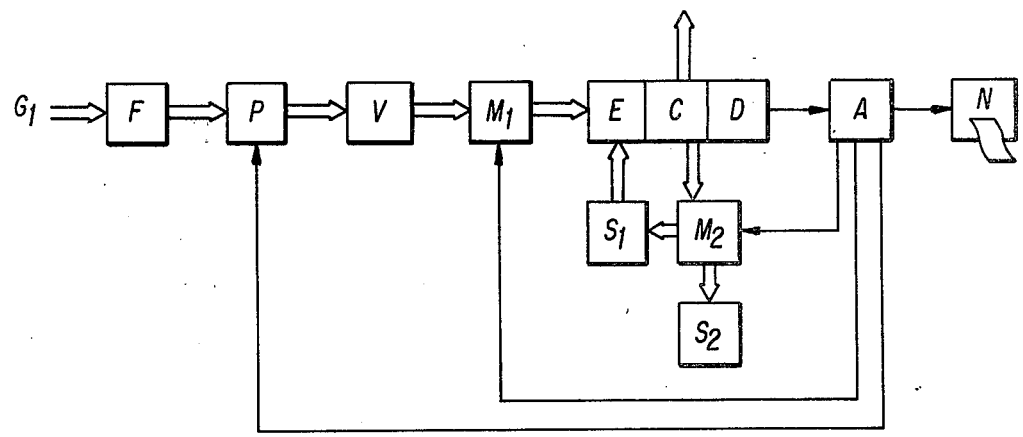
Figure 2:
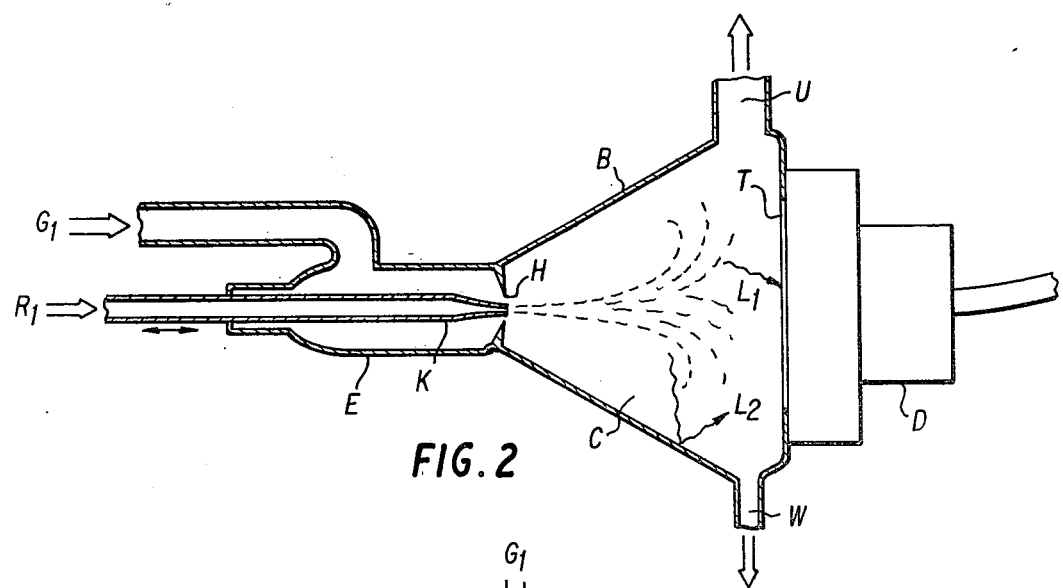
Figure 3:
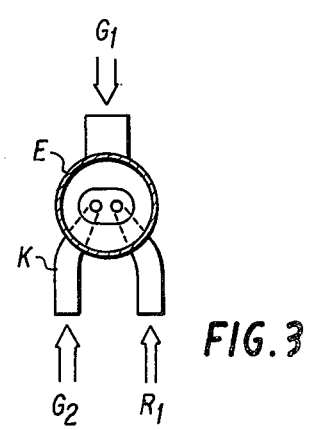
FIG. 3 shows the front view of an ejector device with two ejector tubes.

12. A method according to claims 10 or 11, in which said flow of sample gas propels said aerosol liquid particles into said reaction chamber.

13. A method according to claim 10, in which said sample gas is a constituent of a gas mixture and the flow of said mixture propels said aerosol liquid particles into said reaction chamber.

14. A method according to claim 13, in which said gas mixture is prepared to either increase or decrease its temperature upon expansion.

15. A method according to claim 10, further comprising the step of adjusting the size of said aerosol liquid particles to optimize reaction with said sample gas.

16. A method according to claim 1, further comprising the steps of reflecting said luminescence from the walls of said reaction chamber.

17. A method according to claim 1, further comprising the steps of filtering said luminescence into separate wave length bands and separately detecting luminescence in each of said bands.

18. A method according to claim 1, further comprising the steps of recycling said used liquid reagent when the concentration of the constituent is below a predetermined value and disposing of said used reagent liquid when the concentration of the constituents is above said predetermined value.

* * * * *